United States Patent [19]
Dunn et al.

[11] 3,985,739
[45] Oct. 12, 1976

[54] 3-HETEROCYCLIC THIOMETHYLCEPHALOSPORINS

[75] Inventors: George L. Dunn, Wayne; John R. E. Hoover, Glenside, both of Pa.

[73] Assignee: SmithKline Corporation, Philadelphia, Pa.

[22] Filed: Oct. 1, 1974

[21] Appl. No.: 510,947

Related U.S. Application Data

[63] Continuation of Ser. No. 289,499, Sept. 15, 1975, Pat. No. 3,855,213, which is a continuation-in-part of Ser. No. 262,903, June 14, 1972, Pat. No. 3,867,380, which is a continuation-in-part of Ser. No. 116,599, Feb. 18, 1971, abandoned, which is a continuation-in-part of Ser. No. 116,598, Feb. 18, 1971, abandoned, which is a continuation-in-part of Ser. No. 99,296, Dec. 17, 1970, abandoned.

[52] U.S. Cl. ............................ 260/243 C; 424/246
[51] Int. Cl.² ..................................... C07D 501/24
[58] Field of Search ............................. 260/243 C

[56] References Cited
UNITED STATES PATENTS

| | | | |
|---|---|---|---|
| 3,516,997 | 6/1970 | Takano et al. | 260/243 C |
| 3,759,904 | 9/1973 | Crast | 260/243 C |
| 3,855,213 | 12/1974 | Dunn et al. | 260/243 C |
| 3,867,380 | 2/1975 | Dunn et al. | 260/243 C |

*Primary Examiner*—Nicholas S. Rizzo
*Assistant Examiner*—Jose Tovar
*Attorney, Agent, or Firm*—Alan D. Lourie; William H. Edgerton

[57] ABSTRACT

Cephalosporin compounds substituted at the 7-position with free or substituted α-amino or hydroxy phenylacetamido and at the 3-position with a heterocyclic thiomethyl group are prepared by displacement of a 3-acetoxymethyl compound with a mercaptoheterocycle or by 7-acylation. The products are antibacterial agents.

4 Claims, No Drawings

3-HETEROCYCLIC THIOMETHYLCEPHALOSPORINS

This is a continuation of application Ser. No. 289,499 filed Sept. 15, 1972, now U.S. Pat. No. 3,855,213, which in turn was a continuation-in-part of copending application Ser. No. 116,599, filed Feb. 18, 1971, now abandoned which was a continuation-in-part of application Ser. No. 99,296, filed Dec. 17, 1970, now abandoned, ad it is also a continuation-in-part of copending application Ser. NO. 262,903, filed June 14, 1972, now U.S. Pat. No. 3,867,380, which is a continuation-in-part of application Ser. No. 116,598, filed Feb. 18, 1971, now abandoned, which application was a continuation-in-part of application Ser. No. 99,296, filed Dec. 17, 1970, now abandoned.

This invention relates to chemical compounds known as cephalosporins, which compounds possess antibacterial activity.

The compounds of this invention are represented by the following structural formula:

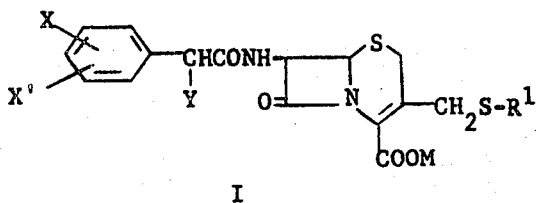

in which:

X and X' are each hydrogen, lower alkyl of 1–4 carbon atoms, lower alkoxy of 1–4 carbon atoms, hydroxy, hydroxmethyl, halo, nitro, amino, mercapto, lower alkylthio of 1–4 carbon atoms, aminomethyl or trifluoromethyl;

Y is $NH_2$ or OH;

$R^1$ is triazolyl, or imidazolyl, each of which is unsubstituted or substituted with 1 or 2 $R^2$ ring substitutes such as lower alkyl of up to 4 carbons, cycloalkyl of up to 6 carbons, alkenyl of up to 6 carbons, lower alkoxy of up to 4 carbons, lower alkoxyalkyl of 2 to 8 carbons, $CF_3$, $NH_2$, alkylamino, dialkylamino, phenyl, methylthio, or halogen, and M is hydrogen or an alkali metal.

Examples of $R^1$ groups are:

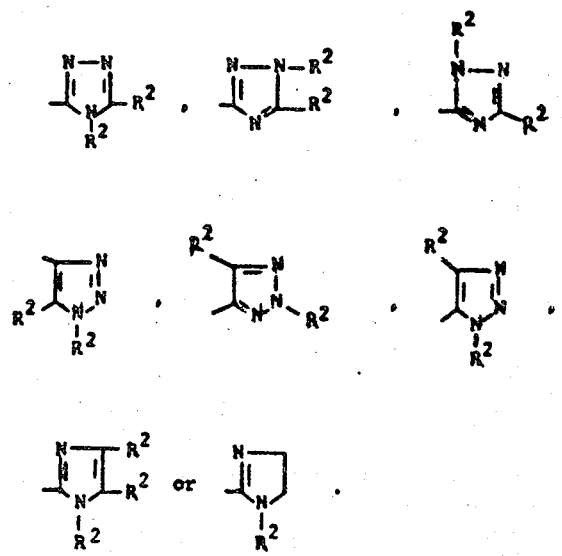

A preferred group of compounds within the scope of Formula I in that in which X is p-HO, X' is H, $R^1$ is triazolyl, and Y is $NH_2$. These compounds have highly advantageous properties as antibacterial agents.

The compounds of the present invention are prepared by reaction of a compound differing from one of Formula I in that the 3substituent is acetoxymethyl rather than $R^1$-thiomethyl with a mercaptoheterocycle. The reaction is preferably conducted at a pH near neutrality. The solvent is preferably water. The reaction may be carried out at temperatures from about room temperature to the boiling point of the solvent, the time of reaction varying with the particular temperature, solvent and reactants. The reaction product is isolated by careful acidification of the reaction mixture and extraction with an appropriate organic solvent. The α-amino group on the phenylglycine starting material should be protected with a readily removable group such as t-butoxycarbonyl, carbobenzyloxy or trichloroethoxycarbonyl. The displacement of the 3-position is then conducted, followed by removal of the protective group in the conventional manner.

The compounds of the invention may also be prepared by acylating the 7-position of the appropriate 7-amino-3-heterocyclic thiomethyl cephalosporin nucleus with a phenylglycine or mandelic acid. Prior to acylation, it is desirable to protect the amino group on the glycine moiety with an easily removable protective group such as t-butoxycarbonyl, benzyloxycarbonyl, trichloroethoxycarbonyl, or similar protective group commonly used in the synthesis of peptides. Similarly, the hydroxy group of the mandelic acid moiety can be protected by conversion to the dichloroacetoxy, tetrahydropyranyloxy, trimethylsilyloxy, formyloxy, or similar known protected derivative. For acylation, the carboxyl group of the acylating agent can be activated by conversion to the acid chloride or to a mixed anhydride with, for example, a lower alkyl chloroformate. The carboxyl group can also be activated by conversion to the 2,4-dinitrophenyl ester. If an ester of the cephalosporin nucleus, for example, the benzhydryl, t-butyl, trichloroethyl, or a benzyl ester, is used, the protected phenylglycine or mandelic acid can be coupled directly to the 7-amino group by using a carbodiimide such dicyclohexylcarbodiimide. Alternatively, the protected phenylglycine or mandelic acid can be activated for condensation with the appropriate cephalosporin nucleus by reacting it first with carbonyldiimidazole or its equivalent.

The starting materials for use in the first process, i.e. 3-displacement of a 7-acylated cephalosporanic acid, are described in the literature of obtainable by known methods. The starting materials for use in the second process, i.e. 7-acylation of a 3-heterocyclic thiomethyl nucleus, are prepared by displacing the 3-acetoxy group of an alkali metal salt of 7-aminocephalosporanic acid (7-ACA) with an alkali metal salt of the heterocyclic thiol in, for example, hot aqueous acetone.

It is recognized that due to the asymmetric α-carbon in the 7-acetamido group optical isomers will exist. The D isomer is the preferred isomer; however, the L isomer and the racemic mixture are also within the scope of this invention.

The starting materials for preparing the products of this invention are known, readily preparable by known methods, or described herein.

The products of this invention are antibacterial agents active against Gram-negative and Gram-positive organisms such as *Staph. aureus, Strep. pyogenes, Strep. faecalis, Diplococcus pneumoniae, E. coli., Klebsiella pneumoniae, Salmonella, Serratia sp., Shigella* and *Enterobacter aerogenes*. A large number of compounds within the scope of Formula I have been prepared and all have had antibacterial activity in an in vitro testing program. Compounds where X is p-OH, X' is H, $R^1$ is triazolyl, and Y is $NH_2$ are especially advantageous in that they exhibit higher blood levels and lower $PD_{50}$'s than related compounds.

The compounds are formulated into injectable formulations in the same manner as other cephalosporin antibiotics. They are administered by injection to prevent and treat bacterial infections in doses which will vary with the nature and severity of the infection and the age, weight, and condition of the subject.

Due to the presence of both an amine group and a carboxylic acid group in certain of the cephalosporin compounds of this invention, it is possible, by standard methods, to prepare both acid and base salts of pharmaceutically acceptable nontoxic acids and bases as well as the zwitterionic forms of the compounds. Salts, when obtained, are readily converted to the zwitterions by known methods. It is to be understood that these salts are included within the scope of this invention.

The following examples are intended to illustrate the preparation of the products of the invention, but are not to be construed as limiting the scope thereof. Temperatures are in degrees Centigrade.

EXAMPLE 1

3-(3,4-Dimethyl-1,2,4-triazol-5-ylthiomethyl)-7-(α-aminophenylacetamido)-3-cephem-4-carboxylic acid To a solution of $NaHCO_3$(4.2 g., 0.05 mol.) in water (50 ml.) was added 7-ACA (6.8 g., 0.025 mol.), water (50 ml.) and acetone (25 ml.). The resulting solution was warmed to 45° and then a solution of 3,4-dimethyl-5-mercapto-1,2,4-triazole (5.0 g., 0.038 mol.) in acetone (50 ml.) and 5% $NaHCO_3$ (10 ml.) was added. The reaction was refluxed until the reaction was completed as determined by the disappearance of the acetoxy carbonyl band in the infrared absorption spectrum. During this time the pH was maintained at ca. 7.6. The solution was cooled to 10° and adjusted to pH 3.5 with 3N HCl. The precipitated product was collected, washed with acetone, and dried to give a 60% yield of 3-(3,4-dimethyl-1,2,4-triazol-5-ylthiomethyl)-7-amino-3-cephem-4-carboxylic acid.

To a cold solution (−10°) of α-t-butoxycarboxamido-phenylacetic acid (2.26 g., 0.013 mol.) and triethylamine (1.4 ml., 0.013 mol.) in dry tetrahydrofuran (50 ml.) was added with stirring isobutyl chloroformate (1.5 ml., 0.013 mol.) over a 10 minute period. To this was added dropwise at −10° a cold solution of the above 7-ACA derivative triethylamine salt [prepared by adding triethylamine (1.5 ml., 0.013 mole) to a suspension of 7-ACA compound (5.0 g., 0.013 mol.) in 40 ml. 50% aq. tetrahydrofuran]. The reaction solution was stirred 1 hour at 0° and 1.5 hours at room temperature. The tetrahydrofuran was evaporated, water added to the mixture, and extracted with ethyl acetate. The organic layer was discarded. The aqueous phase was cooled, layered with ethyl acetate, and acidified to pH 3 using 3N HCl. The phases was separated and the aqueous phase was extracted with ethyl acetate. Evaporation of the combined and dried organic layers gave a solid. Trituration with ether-petroleum ether followed by recrystallization from methylene chloride-ether gave the pure t-butoxycarbonyl derivative.

The above product (6.5 g.) was added to cold trifluoroacetic acid (65 ml.) and stirred at 0°. The solution was poured slowly into a large volume of ether and the precipitated trifluoroacetate salt was collected. Alternatively, the trifluoroacetate salt may be isolated by evaporating the excess trifluoroacetic acid and triturating the residue with ether.

The trifluoroacetate salt (5.3 g.) was dissolved in water (25 ml.) and 15 g. of a polystyrene-amine ion-exchange resin, Amberlite IR-45, was added. After stirring 1 hour at room temperature the resin was filtered off and the aqueous solution was lyophilized to yield the title compound.

An alternative procedure to obtain the zwitterion involved dissolution of the tirfluoroacetate salt in water, addition of methyl isobutyl ketone (MIBK) and, while stirring, adjustment of the solution to pH 4 using tri-n-butylamine. The solid product was collected, washed with MIBK and ethyl acetate, and dried. Calculated for $C_{20}H_{22}N_6O_4S_2 \cdot 1.5H_2O$: C, 47.89; H, 5.02; N, 16.75; Found: C, 48.03; H, 4.66; N, 16.75.

EXAMPLE 2

7-(α-Aminophenylacetamido)-3-(1,2,4-triazol-3-ylthiomethyl)-3-cephem-4-carboxylic acid When 3-mercapto-1,2,4-triazole was reacted according to the procedure of Example 1, the title compound was obtained; m.p. 185 (dec.). Calculated for $C_{18}H_{18}N_6O_4S_2 \cdot H_2O$: C, 46.54; H, 4.34; N, 18.09; Found: C, 46.69; H, 4.34; N, 17.77.

EXAMPLE 3

7-(α-Aminophenylacetamido)-3-(2-methyl-1,2,4-triazole-3-ylthiomethyl)-3-cephem-4-carboxylic acid 3-Mercapto-2-methyl-1,2,4-triazole was reacted according to the procedure of Example 1 to yield the title compound; m.p. 220° (dec.); Calculated for $C_{19}H_{20}N_6O_4S_2 \cdot \frac{1}{2} H_2O$: C, 48.60; H, 4.51; N, 17.90; Found: C, 48.82; H, 4.42; N, 17.78.

EXAMPLE 4

7-(α-Aminophenylacetamido)-3-(4-methyl-1,2,4-triazole-3-ylthiomethyl)-3-cephem-4-carboxylic acid When 3-mercapto-4-methyl-1,2,4-triazole was used in the procedure of Example 1, the title compound was obtained. Calculated for $C_{19}H_{20}N_6O_4S_2 \cdot 2H_2O$: C, 45.96; H, 4.87; N, 16.92; Found: C, 45.51; H, 4.47; N, 16.60.

EXAMPLE 5

7-(α-Aminophenylacetamido)-3-(5-methyl-1,2,4-triazole-3-ylthiomethyl)-3-cephem-4-carboxylic acid The title compound was obtained when 3-mercapto-5-methyl-1,2,4-triazole was used in the procedure of Example 1. Calculated for $C_{19}H_{20}N_6O_4S_2 \cdot 1.25 H_2O$: C, 47.24; H, 4.69; N, 17.29; Found: C, 47.39; H, 4.81; N, 16.80.

EXAMPLE 6

7-(α-Aminophenylacetamido)-3-(4-methyl-5-trifluoromethyl-1,2,4-triazol-3-ylthiomethyl)-3-cephem-4-carboxylic acid When 3-mercapto-4-methyl-5-trifluoromethyl-1,2,4-triazole was used in the procedure of Example 1, the title compound was obtained; m.p. 162°–165° (dec.); Calculated for $C_{20}H_{19}F_3N_6O_4S_2 \cdot 1.5H_2O$: C, 43.24; H, 3.99; N, 15.13; Found: C, 43.63; H, 3.61; N, 14.70.

EXAMPLE 7

7-(α-Aminophenylacetamido)-3-(4-ethyl-1,2,4-triazol-3-ylthiomethyl)-3-cephem-4-carboxylic acid When 4-ethyl-3-mercapto-1,2,4-triazole was reacted according to the procedure of Example 1 the title compound was obtained. Calculated for $C_{20}H_{22}N_6O_4S_2 \cdot 2H_2O$: C, 47.05; H, 5.13; N, 16.46; Found: C, 47.18; H, 4.57; N, 16.09.

EXAMPLE 8

When the appropriately substituted 3-mercapto-1,2,4-triazole was substituted for 3,4-dimethyl-5-mercapto-1,2,4-triazole in the procedure of Example 1 the following cephalosporins were obtained:

7-(α-aminophenylacetamido)-3-(1-ethyl-1,2,4-triazole-3-ylthiomethyl)-3-cephem-4-carboxylic acid Calculaed for $C_{20}H_{22}N_6O_4S_2 \cdot 1.5\ H_2O$: C, 47.89; H, 5.02; N, 16.76; Found: C, 47.64; H, 4.63; N, 16.79.

7-(α-aminophenylacetamido)-3-(1-isopropyl-1,2,4-triazol-3-ylthiomethyl)-3-cephem-4-carboxylic acid Calculated for $C_{21}H_{24}N_6O_4S_2 \cdot 0.5\ H_2O$: C, 50.69; H, 5.06; N, 16.89; Found: C, 50.43; H, 5.31; N, 17.14.

7-(α-aminophenylacetamido)-3-(4-n-propyl-1,2,4-triazol-3-ylthiomethyl)-3-cephem-4-carboxylic acid Calculated for $C_{21}H_{24}N_6O_4S_2 \cdot 1.5\ H_2O$: C, 48.92; H, 5.28; N, 16.30; Found: C, 48.95; H, 4.98; N, 16.11.

7-(α-aminophenylacetamido)-3-(4-isopropyl-1,2,4-triazol-3-ylthiomethyl)-3-cephem-4-carboxylic acid Calculated for $C_{21}H_{24}N_6O_4S_2 \cdot 1.5\ H_2O$: C, 48.92; H, 5.28; N, 16.30; Found: C, 49.35; H, 4.90; N, 15.92.

7-(α-aminophenylacetamido)-3-(4-n-butyl-1,2,4-triazol-3-ylthiomethyl)-3-cephem-4-carboxylic acid Calculated for $C_{22}H_{26}N_6O_4S_2 \cdot 1.25\ H_2O$: C, 50.32; H, 5.47; N, 16.00; Found: C, 50.48; H, 5.24; N, 15.65.

7-(α-aminophenylacetamido)-3-(4-allyl-1,2,4-triazol-3-ylthiomethyl)-3-cephem-4-carboxylic acid Calculated for $C_{21}H_{22}N_6O_4S_2 \cdot 1.25\ H_2O$: C, 49.54; H, 4.85; N, 16.51; Found: C, 49.82; H, 4.56; N, 16.03.

7-(α-aminophenylacetamido)-3-(5-ethyl-1,2,4-triazol-3-ylthiomethyl)-3-cephem-4-carboxylic acid Calculated for $C_{20}H_{22}N_6O_4S_2 \cdot 2\ H_2O$: C, 47.05; H, 5.13; 16.46; Found C, 46.85; H, 4.72; N, 16.22.

7-(α-aminophenylacetamido)-3-(5-n-propyl-1,2,4-triazol-3-ylthiomethyl)-3-cephem-4-carboxylic acid Calculated for $C_{21}H_{24}N_6O_4S_2 1.25\ H_2O$: C, 49.35; H, 5.23; N, 16.44; Found: C, 49.74; H, 5.40; N, 15.94.

7-(α-aminophenylacetamido)-3-(5-isopropyl-1,2,4-triazol-3-ylthiomethyl)-3-cephem-4-carboxylic acid Calculated for $C_{21}H_{24}N_6O_4S_2 \cdot H_2O$: C, 49.79; H, 5.17; N, 16.59; Found: C, 49.98; H, 5.03; N, 16.59.

7-(α-aminophenylacetamido)-3-(5-cyclopropyl-1,2,4-triazol-3-ylthiomethyl)-3-cephem-4-carboxylic acid Calculated for $C_{21}H_{22}N_6O_4S_2 \cdot H_2O$: C, 49.99; H, 4.79; N, 16.66; Found: C, 50.32; H, 4.61; N, 16.34.

7-(α-aminophenylacetamido)-3-(5-methoxymethyl-1,2,4-triazol-3-ylthiomethyl)-3-cephem-4-carboxylic acid Calculated for $C_{20}H_{22}N_6O_5S_2 \cdot 1.5\ H_2O$: C, 46.41; H, 4.87; N, 16.24; Found: C, 45.69; H, 4.70; N, 15.64.

7-(α-aminophenylacetamido)-3-(1-ethyl-5-methyl-1,2,4-triazol-3-ylthiomethyl)-3-cephem-4-carboxylic acid Calculated for $C_{21}H_{24}N_6O_4S_2 \cdot 0.75\ H_2O$: C, 50.23; H, 5.11; N, 16.40; Found: C, 50.23; H, 5.12; N, 16.74.

7-(α-aminophenylacetamido)-3-(4-ethyl-5-methyl-1,2,4-triazol-3-ylthiomethyl)-3-cephem-4-carboxylic acid Calculated for $C_{21}H_{24}N_6O_4S_2 \cdot 2\ H_2O$: C, 48.08; H, 5.38; N, 16.02 Found: C, 48.30; H, 4.98; N, 15.39.

7-(α-aminophenylacetamido)-3-(1,3-dimethyl-1,2,4-triazol-5-ylthiomethyl)-3-cephem-4-carboxylic acid Calculated for $C_{20}H_{22}N_6O_4S_2 \cdot H_2O$: C, 48.77; H, 4.91; N, 17.06; Found: C, 49.06; H, 4.65; N, 16.89.

EXAMPLE 9

7-(α-Aminophenylacetamido)-3-(1,2,3-triazol-4-ylthiomethyl)-3-cephem-4-carboxylic acid When 5-mercapto-1,2,3-triazole was reacted according to the procedure of Example 1 the title compound was prepared as the trifluoroacetate salt. Calculated for $C_{18}H_{18}N_6O_4S_2 \cdot C_2HF_3O_2$: C, 42.86; H, 3.42; N, 14.89; Found: C, 42.83; H, 3.63; N, 15.13.

EXAMPLE 10

7-(α-Amino-p-hydroxyphenylacetamido)-3-(1,2,3-triazol-4-ylthiomethyl)-3-cephem-4-carboxylic acid To a stirred solution of N-t-butoxycarbonyl-p-hydroxyphenylglycine (10.75 g, 0.0375 mol) in dry THF (150 ml) was added triethylamine (5.2 ml, 0.0375 mol). The mixture was cooled to −10° and then isobutyl chloroformate (4.92 ml, 0.0375 mol) was added dropwise over a 10 minute period. The reaction mixture was stirred at −10° for 70 minutes and then a cold solution of 7-ACA (10.1 g, 0.0375 mol) in 50% aqueous THF (140 ml) and triethylamine (6.75, 0.0487 mol) was added over a 15 minute period. The reaction was stirred at −5 to 0° for one hour and at room temperature for 2 hours. The organic solvents were evaporated and water (150 ml) was added to the aqueous residue. The solution was extracted with ethyl acetate and the aqueous phase was separated, covered with fresh ethyl acetate, acidified to pH 2.8, and filtered. The phases were separated and the acidic solution reextracted with ethyl acetate. The extracts of the acidified aqueous solution were combined, dried, and evaporated to give 7-(α-amino-p-hydroxyphenylacetamido)cephalosporanic acid.

A mixture of the above product (3.0 g, 0.00493 mol) in pH 6.4 buffer (30 ml) was treated with NaHCO$_3$ (1.085 g, 0.01233 mol) and then 4-mercapto-1,2,3-triazole (0.748 g, 0.0074 mol). The solution was warmed to 70° and stirred at 70 ± 3° for 2.75 hours. The solution was cooled, filtered, and acidified to pH 2.5 producing a residue. The solvents were decanted and the residue washed with water. The product was dissolved in ethyl acetate, washed with water, dried, and evaporated to the N-protected product which was reprecipitated from acetone-chloroform.

The protected product was stirred at 0° to 5° with a 9:1 trifluoroacetic acid:anisole solution for 70 minutes. The solvents were evaporated and the residue was poured with rapid stirring into ether (350 ml). The product was collected, washed with ether and triturated with acetone.

Calculated for $C_{18}H_{18}N_6O_5S_2 \cdot 2$ H$_2$O: C, 43.37; H, 4.45; N, 16.86; Found: C, 43.67; H, 4.14; N, 16.62.

EXAMPLE 11

Use of the t-butoxycarbonyl derivative of a p-chloro-α-aminophenylacetamido, p-nitro-α-aminophenylacetamido, 3,4-dimethoxy-α-aminophenylacetamido, 3-trifluoromethyl-α-aminophenylacetamido, α,p-diaminophenylacetamido or p-methyl-α-aminophenylacetmidocephalosporanic acid and 3,4-dimethyl-5-mercapto-1,2,4-triazole in the procedure of Example 10 gives the corresponding 7-(α-amino substituted phenylacetamido)-3-(3,4-dimethyl-1,2,4-triazol-5-ylthiomethyl)-3-cephem-4-carboxylic acid.

EXAMPLE 12

When an equivalent amount of the appropriate heterocyclic thiol is substituted for 3,4-dimethyl-5-mercapto-1,2,4-triazole in the procedure of Example 1, the following cephalosporins are obtained:
3-(1-methylimidazol-2-ylthiomethyl)-7-(α-aminophenyl-acetamido)-3-cephem-4-carboxylic acid
3-(1,5-dimethylimidazol-2-ylthiomethyl)-7-(α-aminophenylacetamido)-3-cephem-4-carboxylic acid
3-(imidazol-2-ylthiomethyl)-7-(α-aminophenylacetamido)-3-cephem-4-carboxylic acid
3-[4(5)-methylimidazol-2-ylthiomethyl]-7-(α-aminophenylacetamido)-3-cephem-4-carboxylic acid
3-(4,5-dimethylimidazol-2-ylthiomethyl)-7-(α-aminophenylacetamido)-3-cephem-4-carboxylic acid

EXAMPLE 13

When an equivalent amount of the t-butoxycarbonyl derivative of 7-(3,4-dichloro-α-aminophenylacetamido)-cephalosporanic acid, 7-(p-hydroxymethyl-α-aminophenylacetamido)cephalosporanic acid, 7-(p-aminomethyl-α-aminophenylacetamido)-cephalosporanic acid, 7-(3,5-dihydroxy-α-aminophenylacetamido)cephalosporanic acid, 7-(3-chloro-4-hydroxy-α-aminophenylacetamido)cephalosporanic acid, 7-(2-chloro-4-hydroxy-α-aminophenylacetamido)cephalosporanic acid, 7-(2-fluoro-4-hydroxy-α-aminophenylacetamido)cephalosporanic acid, 7-(3-fluoro-4-hydroxy-α-aminophenylacetamido)cephalosporanic acid, 7-(4-isopropyl-α-aminophenylacetamido)cephalosporanic acid, 7-(4-bromo-αaminophenylacetamido)cephalosporanic acid, 7-(3-fluoro-α-aminophenylacetamido)cephalosporanic acid, or 7-(2-chloro-α-aminophenylacetamido)cephalosporanic acid and 3,4-dimethyl-5-mercapto-1,2,4-triazole are substituted for the starting materials in the procedure of Example 10, the corresponding 7-substituted α-aminophenylacetamido-3-(3,4-dimethyl-1,2,4-triazolyl-5-ylthiomethyl)-3-cephem-4-carboxylic acid is obtained.

EXAMPLE 14

Use of the t-butoxycarbonyl derivative of a p-chloro-α-aminophenylacetamido, p-hydroxy-α-aminophenylacetamido, p-nitro-α-aminophenylacetamido, p-hydroxy-m-methoxy-α-aminophenylacetamido, 3,4-dimethoxy-α-aminophenylacetamido, p-methoxy-m-hydroxy-α-aminophenylacetamido, 3-trifluoromethyl-α-aminophenylacetamido, 3,4-dihydroxy-α-aminophenylacetamido, α,p-diaminophenylacetamido, p-hydroxymethyl-α-aminophenylacetamido, p-aminomethyl-α-aminophenylacetamido, 3,5-dihydroxy-α-aminophenylacetamido, 2-chloro-4-hydroxy-α-aminophenylacetamido, 3-chloro-4-hydroxy-α-aminophenylacetamido, 2-fluoro-4-hydroxy-α-aminophenylacetamido, 3-fluoro-4-hydroxy-α-aminophenylacetamido, or p-methyl-α-aminophenylacetamidocephalosporanic acid and 5-methyl-3-mercapto-1,2,4-triazole in the procedure of Example 10 gives the corresponding 7-(α-amino substituted phenylacetamido)-3-(5-methyl-1,2,4-triazol-3-ylthiomethyl)-3-cephem-4-carboxylic acid.

EXAMPLE 15

Use of 1-methyl-5-mercapto-1,2,3-triazole, 1-ethyl-5-mercapto-1,2,3-triazole, 4-methyl-5-mercapto-1,2,3-triazole, 1-methyl-4-mercapto-1,2,3-triazole, 2-methyl-4-mercapto-1,2,3-triazole, 4,5-diethyl-3-mercapto-1,2,4-triazole, 4-ethyl-3-mercapto-5-methyl-1,2,4-triazole, or 5-ethyl-3-mercapto-4-methyl-1,2,4-triazole in the procedure of Example 1 gives the corresponding 7-(α-aminophenylacetamido)-3-(heterocyclic thiomethyl)-3-cephem-4-carboxylic acid.

EXAMPLE 16

Use of 3-mercapto-1-n-propyl-1,2,4-triazole, 3-mercapto-2-n-propyl-1,2,4-triazole, 3-mercapto-4,5-di-n-propyl-1,2,4-triazole, 3-mercapto-2-isopropyl-1,2,4-triazole, 3-mercapto-4,5-diisopropyl-1,2,4,-triazole, 1-allyl-3-mercapto-1,2,4-triazole, 2-allyl-3-mercapto-1,2,4-triazole, 5-allyl-3-mercapto-1,2,4-triazole, 4,5-diallyl-3-mercapto-1,2,4-triazole, 1-cyclopropyl-3-mercapto-1,2,4-triazole, 2-cyclopropyl-3-mercapto-1,2,4-triazole, 4cyclopropyl-3-mercapto-1,2,4-triazole, and 4,5-dicyclopropyl-3-mercapto-1,2,4-triazole in the procedure of Example 1 gives the corresponding 7-(α-aminophenylacetamido)-3-substituted-1,2,4-triazol-3-thiomethyl)-3-cephem-4-carboxylic acid.

EXAMPLE 17

When the t-butoxycarbonyl derivative of p-hydroxyphenylglycine is reacted with the appropriate 7-amino-3-heterocyclicthiomethyl-3-cephem-4-carboxylic acid according to the procedure of Example 1 the following compounds are obtained:
7-(α-amino-p-hydroxyphenylacetamido)-3-(4-methyl-1,2,4-triazol-3-ylthiomethyl)-3-cephem-4-carboxylic acid
7-(α-amino-p-hydroxyphenylacetamido)-3-(4,5-dimethyl-1,2,4-triazol-3-ylthiomethyl)-3-cephem-4-carboxylic acid 7-(α-amino-p-hydroxyphenylacetamido)-3-(1-methyl-1,2,3-triazol-4-ylthiomethyl)-3-cephem-4-carboxylic acid 7-(α-amino-p-hydroxyphenylacetamido)-3-(1-methyl-1,2,3-triazol-5-ylthiomethyl)-3-cephem-4-carboxylic acid 7-(α-amino-p-hydroxyphenylacetamido)-3-(2-methyl-1,2,3-triazol-4-ylthiomethyl)-3-cephem-4-carboxylic acid

EXAMPLE 18

When 3,4-dihydroxyphenylglycine is substituted for p-hydroxyphenylglycine in Example 17, the corresponding 7-(α-amino-3,4-dihydroxyphenylacetamido)-3-(heterocyclicthiomethyl)-3-cephem-4-carboxylic acid is obtained.

EXAMPLE 19

When 4-hydroxy-3-methoxyphenylglycine is substituted for p-hydoxyphenylglycine in Example 17, the corresponding 7-(α-amino-4-hydroxy-3-methoxyphenylacetamido) 3-heterocyclicthiomethyl-3-cephem-4-carboxylic acid is formed.

EXAMPLE 20

When 3-hydroxy-4-methoxyphenylglycine is substituted for p-hydroxyphenylglycine in Example 17, the corresponding 7-(α-amino-3-hydroxy-4-methoxyphenylacetamido)-3-heterocyclicthiomethyl-3-cephem-4-carboxylic acid is obtained.

EXAMPLE 21

The compounds enumerated in Example 17 are also prepared by reacting 7-(α-amino-p-hydroxyphenylacetamido)-cephalosporanic acid with the appropriate mercaptotriazole according to the procedure of Example 10.

EXAMPLE 22

An injectable pharmaceutical composition is prepared by dissolving 500 mg. of sodium 7-(α-amino-p-hydroxphenyl-acetamido)-3-1,2,3-triazol-5-ylthiomethyl)-3-cephem-4-carboxylate in 2 ml. of sterile water on normal saline solution.

Any of the above disclosed cephalosporins may be formulated in a similar manner.

EXAMPLE 23

An antibacterial capsule has the following components: cephalosporin (500 mg.), lactose (250 mg.) and magnesium stearate (75 mg.).

EXAMPLE 24

7-Mandelamido-3-(1,2,4-triazol-3-ylthiomethyl)-3-cephem-4-carboxylic acid

A solution of 7-mandelamidocephalosporanic acid methanolate (5.66 g, 12.9 mmol), 3-mercapto-1H-1,2,4-triazole (1.38 g, 13.7 mmol), and sodium bicarbonate (1.14 g, 13.7 mmol) in pH 6.4 phosphate buffer (300 ml) was stirred under nitrogen at 56° for 21 hours. When an internal temperature of 45° was attained, additional sodium bicarbonate (1.14 g, 13.7 mmol) was added. The reaction was cooled, layered with ethyl acetate, and acidified to pH 2 with 3N HCl. The phases were separated and the aqueous phase was extracted with ethyl acetate. The combined extracts were dried ($Na_2SO_4$) and concentrated in vacuo to give the crude free acid.

This free acid was chromatographed on silica gel (100 g) which had been deactivated with water (15 g). The desired product was eluted with 3% methanol in chloroform.

The sodium salt was prepared by dissolution of the free acid in cold methanol and adjustment of the solution to pH 6.9 with a 5% methanolic sodium methoxide solution. The salt was precipitated with the addition of ether; mp 210° (dec). Calculated for $C_{18}H_{16}N_5O_4S_2$·Na·H$_2$O: C, 44.34; H, 3.72; N, 14.37; Found: C, 44.20; H, 4.18; N, 14.17.

EXAMPLE 25

7-Mandelamido-3-(4-methyl-3-trifluoromethyl-1,2,4-triazol-5-ylthiomethyl-3-cephem-4-carboxylic acid To a cooled solution of O-tetrahydropyranylmandelic acid (4.73 g, 0.02 mol) and N-hydroxysuccinimide (2.3 g, 0.02 mol) in anhydrous tetrahydrofuran was added dicyclohexylcarbodiimide (4.12 g, 0.02 mol). After stirring 7 hours at ice bath temperature, the reaction was allowed to stand at room temperature overnight. The dicyclohexylurea was removed by filtration and the filtrate was evaporated to yield the succinimide ester.

7-Amino-3-(4-methyl-3-trifluoromethyl-1,2,4-triazol-5-ylthiomethyl)-3-cephem-4-carboxylic acid was prepared according to the procedure of Example 1 by substituting 5-mercapto-4-methyl-3-trifluoromethyl-1,2,4-triazole for 3,4-dimethyl-5-mercapto-1,2,4-triazole.

To a cooled solution of this 7-aminocephem compound (6.3 g, 0.016 mol) in dry pyridine (80 ml) containing triethylamine (3.4 g) was added the succinimide ester (5.5 g, 0.016 mol). The reaction was stirred for 3 hours at room temperature and then poured into water (600 ml) that had been acidified to pH 2. The precipitated solid was collected, dissolved in ethyl acetate, and separated from insoluble material. Concentration gave the product which was purified further by trituration with ether-petroleum ether.

The above product (4.9 g, 0.0078 mol) was stirred in 14 ml ice cold trifluoroacetic acid for 45 minutes. The trifluoroacetic acid was removed in vacuo and the residue triturated with ether to yield the solid title compound; mp 135°–318°. Calculated for $C_{20}H_{18}F_3N_5O_5S_2$·½H$_2$O: C, 46.63; H, 4.09; N, 12.36; Found: C, 46.27; H, 3.84; N, 12.56.

EXAMPLE 26

7-Mandelamido-3-(1-methylimidazol-2-ylthiomethyl)-3-cephem-4-carboxylic acid

A solution of 7.62 g of 7-mandelamidocephalosporanic acid methanolate, 2.94 g of NaHCO$_3$, and 3.0 g of 2-mercapto-1-methylimidazole in a mixture of 50 ml of water and 25 ml of acetone was maintained at reflux for 90 minutes. The solution was diluted with 75 ml of water and adjusted to pH 3.0. The precipitate produced was filtered and washed with water to give 1.72 g of product after drying; mp 168°–71° (dec).

EXAMPLE 27

7-Mandelamido-3-(4-methyl-1,2,4-triazol-3-ylthiomethyl)-3-cephem-4-carboxylic acid 7-Amino-3-(4-methyl-1,2,4-triazol-3-ylthiomethyl)-3-cephem-4-carboxylic acid was prepared from 7-ACA and 3-mercapto-4-methyl-1,2,4-triazole according to the first paragraph of Example 1.

The above product (6.0 g, 18.3 mmol) was dissolved in 3% NaHCO$_3$ (138 ml) and acetone (138 ml). After cooling to −15°, a solution of o-dichloroacetylmandeloyl chloride (10.3 g, 36.6 mmol) in dry acetone (70 ml) was added over a 35 minute period. After 45 minutes the solution was allowed to rise to 0° and then the pH was adjusted to 5 with 10% NaOH. After 15 minutes a brown solid was filtered from the aqueous solution and disgarded. The aqueous layer was washed with ether and then was acidified to pH 3.8. A solid was collected and washed with acetone to give a solution which was concentrated. The residue was taken up in methanol and was precipitated with ether. The solid was dissolved in methanol and the pH was raised to 9.7 with dilute methanolic sodium methoxide. After 13 minutes the pH was adjusted to 7.3 using 2-ethylhexanoic acid and the sodium salt of the title compound was precipitated by the addition of ether.

Calculated for $C_{19}H_{19}N_5O_5S_2Na.2.5H_2O$: C, 43.18; H, 4.39; N, 13.25: Found: C, 43.15; H, 3.89; N, 13.16.

EXAMPLE 28

7-Mandelamido-3-(3,4-dimethyl-1,2,4-triazol-5-ylthiomethyl)-3-cephem-4-carboxylic acid 7-Amino-3-(3,4-dimethyl-1,2,4-triazol-5-ylthiomethyl)-3-cephem-4-carboxylic acid was prepared in the first paragraph of the procedure of Example 1. This product was acylated by the succinimide ester method of Example 25. After stirring the acylation reaction mixture 2.5 hours, the mixture was filtered and poured into a large volume of ether. The precipitated solid was separated, dissolved in chloroform, and washed with water. After drying, the solution was evaporated to give the THP protected product. The product (3.0 g, 5.36 mmol) was dissolved in methylene chloride (35 ml), cooled in ice, and treated 10 minutes with ethereal hydrochloric acid (15 ml) during which time the hydrochloride salt of the title compound was formed and collected; mp 110° (dec). Calculated for $C_{20}H_{21}N_5O_5S_2.HCl.H_2O$: C, 46.60; H, 5.15; N, 12.35; Found: C, 46.85; H, 5.27; N, 12.28.

EXAMPLE 29

7-Mandelamido-3-(2-methyl-1,2,4-triazol-3-ylthiomethyl)-3-cephem-4-carboxylic acid The tital compound as its sodium salt was prepared when the procedure of Example 27 was followed using 3-mercapto-2-methyl-1,2,4-triazole. Calculated for $C_{19}H_{18}N_5O_5S_2Na.2H_2O.0.1\ C_4H_8O_2$: C, 43.93; H, 4.27; N, 13.48; Found: C, 44.51; H, 3.99; N, 13.08.

EXAMPLE 30

7-Mandelamido-3-(4-ethyl-1,2,4-triazol-3-ylthiomethyl)-3-cephem-4-carboxylic acid When the procedure of Example 27 was used with 4-ethyl-3-mercapto-1,2,4-triazole, the title compound was obtained as its sodium salt. Calculated for $C_{20}H_{20}N_5O_5S_2Na.1.5H_2O$: C, 45.80; H, 4.42; N, 13.35; Found: C, 45.93; H, 4.16; N, 13.10.

EXAMPLE 31

When 7-ACA, the appropriate mercaptotriazole, and α-dichloroacetylmandeloyl chloride was reacted according to the procedure of Example 27 the following compounds were obtained:

7Mandelamido-3-(5-n-propyl-1,2,4-triazol-3-ylthiomethyl)-3-cephem-4-carboxylic acid Calculated for $C_{21}H_{22}N_5O_5S_2Na.1.5H_2O$: C, 46.83; H, 4.68; N, 13.00; Found: C, 46.62; H, 4.36; N, 12.94.

7-Mandelamido-3-(5-cyclopropyl-1,2,4-triazol-3-ylthiomethyl)-3-cephem-4-carboxylic acid Calculated for $C_{21}H_{20}N_5O_5S_2Na.1.5H_2O$: C, 47.01; H, 4.32; N, 13.05; Found: C, 47.26, H, 4.08; N, 13.00.

7-Mandelamido-3-(5-methoxymethyl-1,2,4-triazol-3-ylthiomethyl)-3-cephem-4-carboxylic acid Calculated for $C_{20}H_{20}N_5O_6S_2Na.1.5H_2O$: C, 44.44; H, 4.29; N, 12.96; Found: C, 44.51; H, 402; N, 12.75.

7-Mandelamido-3-(4-n-propyl-1,2,4-triazol-3-ylthiomethyl)-3-cephem-4-carboxylic acid Calculated for $C_{21}H_{22}N_5O_5S_2Na.2H_2O$: C, 46.06; H, 4.79; N, 12.99; Found: C, 45.98; H, 4.26; N, 12.43.

7-Mandelamido-3-(4-i-propyl-1,2,4-triazol-3-ylthiomethyl)-3-cephem-4-carboxylic acid;

Calculated for $C_{21}H_{22}N_5O_5S_2Na.1.5H_2O$: C, 46.83; H, 4.68; N, 13.00; Found: C, 46.94; H, 4.31; N, 12.93.

7-Mandelamido-3-(4-allyl-1,2,4-triazol-3-ylthiomethyl)-3-cephem-4-carboxylic acid Calculated for $C_{21}H_{20}N_5O_5S_2Na.1.75H_2O$: C, 46.62; H, 4.38; N, 12.94; Found: C, 46.68; H, 4.02; N, 12.55.

7Mandelamido-3-(1-methyl-1,2,4-triazol-3-ylthiomethyl)-3-cephem-4-carboxylic acid Calculated for $C_{18}H_{18}N_5O_5S_2Na.1.75H_2O$: C, 44.31; H, 4.21; N, 13.60; Found: C, 44.76; H, 4.01; N, 13.04.

7-Mandelamido-3-(1-i-propyl-1,2,4-triazol-3-ylthiomethyl)-3-cephem-4-carboxylic acid Calculated for $C_{21}H_{22}N_5O_5S_2Na.1.25H_2O$: C, 47.23; H, 4.62; N, 13.11; Found: C, 47.53; H, 4.39; N, 12.57.

7-Mandelamido-3-(2,5-dimethyl-1,2,4-triazol-3-ylthiomethyl)-3-cephem-4-carboxylic acid Calculated for $C_{20}H_{20}N_5O_5S_2Na.1.5H_2O$: C, 45.80; H, 4.42; N, 13.35; Found: C, 46.23; H, 4.11; N, 12.75.

7-Mandelamido-3-(1-ethyl-5-methyl-1,2,4-triazol-3-ylthiomethyl)-3-cephem-4-caboxylic acid Calculated for $C_{21}H_{22}N_5O_5S_2Na.H_2O$: C, 47.63; H, 4.57; N, 13.22; Found: C, 47.50; H, 4.50; N, 12.90.

7-Mandelamido-3-(5-ethyl-1,2,4-triazol-3-ylthiomethyl)-3-cephem-4-carboxylic acid Calculated for $C_{20}H_{20}N_5O_5S_2Na.1.25H_2O$: C, 44.64; H, 4.59; N, 13.02; Found: C, 44.37; H, 4.10; N, 12.48.

7-Mandelamido-3-(1-ethyl-1,2,4-triazol-3-ylthiomethyl)-3-cephem-4-carboxylic acid Calculated for $C_{20}H_{20}N_5O_5S_2Na.H_2O$: C, 46.60; H, 4.30; N, 13.58; Found: C, 46.95; H, 4.00; N, 13.71.

7-Mandelamido-3-(4-ethyl-5-methyl-1,2,4-triazol-3-ylthiomethyl)-3-cephem-4-carboxylic acid Calculated for $C_{21}H_{22}N_5O_5S_2Na \cdot 1.75H_2O$: C, 46.44; H, 4.73; N, 12.90; Found: C, 46.74; H, 4.40; N, 12.46.

7-Mandelamido-3-(1,2,3-triazol-4-ylthiomethyl)-3-cephem-4-carboxylic acid

Calculated for $C_{18}H_{16}N_5O_5S_2Na \cdot 2H_2O$: C, 42.77; H, 3.99; N, 13.85; Found: C, 42.46; H, 3.46; N, 13.57.

7-Mandelamido-3-(1-methyl-1,2,3-triazol-5-ylthiomethyl)-3-cephem-4-carboxylic acid Calculated for $C_{19}H_{18}N_5O_5S_2Na \cdot 2H_2O$: C, 43.93; H, 4.27; N, 13.48; Found: C, 43.69; H, 3.81; N, 13.21.

EXAMPLE 32

3-Mercapto-5-methyl-1,2,4-triazole was reacted according to the procedure of Example 27, to yield 7-mandelamido-3-(5-methyl-1,2,4-triazol-3-ylthiomethyl)-3-cephem-4-carboxylic acid. The sodium salt was prepared using the sodium methoxide method of Example 23.

Calculated for $C_{19}H_{18}N_5O_5S_2Na \cdot 2H_2O$: C, 43.93; H, 4.27; N, 13.48; Found: C, 43.55; H, 3.92; N, 13.02.

EXAMPLE 33

When an equivalent amount of 4-mercapto-2-methyl-1,2,3-triazole, 5-mercapto-4-methyl-1,2,3-triazole, 4-mercapto-1-methyl-1,2,3-triazole, 2-ethyl-3-mercapto-1,2,4-triazole, or 3-mercapto-4,5-diethyl-4H-1,2,4-triazole is substituted for 3-mercapto-4-methyl-1,2,4-triazole in the procedure of Example 27 the following cephalosporins are obtained:

3-(2-methyl-1,2,3-triazol-4-ylthiomethyl)-7-mandelamido-3-cephem-4-carboxylic acid 3-(4-methyl-1,2,3-triazol-5-ylthiomethyl)-7-mandelamido-3-cephem-4-carboxylic acid 3-(1-Methyl-1,2,3-triazol-4-ylthiomethyl)-7-mandelamido-3-cephem-4-carboxylic acid 3-(2-Ethyl-1,2,4-triazol-3-ylthiomethyl)-7-mandelamido-3-cephem-4-carboxylic acid 3-(4,5-diethyl-4H-1,2,4-triazol-3-ylthiomethyl)-7-mandelamido-3-cephem-4-carboxylic acid

EXAMPLE 34

When an equivalent amount of the appropriate heterocyclic thiol is substituted for 3-mercapto-4-methyl-1,2,4-triazole in the procedure of Example 27, the following cephalosporins are obtained.

3-(1,5-Dimethylimidazol-2-ylthiomethyl)-7-mandelamido-3-cephem-4-carboxylic acid 3(Imidazol-2-ylthiomethyl)-7-mandelamido-3-cephem-4-carboxylic acid 3-[4(5)-Methylimidazol-2-ylthiomethyl]-7-mandelamido-3-cephem-4-carboxylic acid 3-(3,4-Dimethylimidazol-2-ylthiomethyl)-7-mandelamido-3-cephem-4-carboxylic acid

EXAMPLE 35

When an equivalent amount of 1-methyl-1H-1,2,4-triazole-5-thiol, 1-phenyl-3-methyl-1H-1,2,4-triazole-5-thiol, 3-phenyl-5-mercapto-1,2,4-triazole, or 5-ethyl-3-mercapto-4-methyl-1,2,4-triazole is substituted for 3-mercapto-4-methyl-1,2,4-triazole in the procedure of Example 27, the corresponding 3-triazolylthiomethyl-7-mandelamido-3-cephem-4-carboxylic acid is obtained.

EXAMPLE 36

When an equivalent amount of 7-(3,4-dichloromandelamido)cephalosporanic acid, 7-(4-methylmandelamido)-cephalosporanic acid, 7-(3,4-dimethoxymandelamido)-cephalosporanic acid, 7-(4-isopropylmandelamido)cephalosporanic acid, 7-(4-bromomandelamido)cephalosporanic acid, 7-(3-fluoromandelamido)cephalosporanic acid, 7-(4-nitromandelamido)-cephalosporanic acid, 7-(2-chloromandelamido)cephalosporanic acid, 7-(4-aminomandelamido)cephalosporanic acid, or 7-(3-trifluoromethylmandelamido)cephalosporanic acid is substituted for 7-mandelamidocephalosporanic acid, and 3-mercapto-5-methyl-1,2,4-triazole is substituted for 3-mercapto-1,2,4-triazole in the procedure of Example 24, the corresponding 7-substituted mandelamido-3-(5-methyl-1,2,4-triazol-3-ylthiomethyl)-3-cephem-4-carboxylic acid is obtained.

EXAMPLE 37

Use of 3-mercapto-1-n-propyl-1,2,4-triazole, 3-mercapto-2-n-propyl-1,2,4-triazole, 3-mercapto-4,5-di-n-propyl-1,2,4-triazole, 3-mercapto-2-isopropyl-1,2,4-triazole, 3-mercapto-5-isopropyl-1,2,4-triazole, 3-mercapto-4,5-diisopropyl-1,2,4-triazole, 1-allyl-3-mercapto-1,2,4-triazole, 2-allyl-3-mercapto-1,2,4-triazole, 5-allyl-3-mercapto-1,2,4-triazole, 4,5-diallyl-3-mercapto-1,2,4-triazole, 1-cyclopropyl-3-mercapto-1,2,4-triazole, 2-cyclopropyl-3-mercapto-1,2,4-triazole, 4-cyclopropyl-3-mercapto-1,2,4-triazole, and 4,5-dicyclopropyl-3-mercapto-1,2,4-triazole in the procedure of Example 27 gives the corresponding 7-mandelamido-3-(substituted-1,2,4-triazol-3-thiomethyl)-3-cephem-4-carboxylic acid.

EXAMPLE 38

When 7-(α-amino-p-hydroxyphenylacetamido)-cephalosporanic acid was reacted with 1-methyl-5-mercaptotetrazole according to the procedure of Example 10, 7-(α-amino-p-hydroxyphenylacetamido)-3-(1-methyltetrazol-5-ylthiomethyl)-3-cephem-4-carboxylic acid was obtained.

Calculated for $C_{18}H_{19}N_7O_5S_2 \cdot H_2O$: C, 43.63; H, 4.07; N, 19.79; Found: C, 43.71; H, 4.26; N, 19.43.

EXAMPLE 39

When the t-butoxycarbonyl derivative of 7-(α-amino-p-hydroxyphenylacetamido)cephalosporanic acid and 5-mercapto-4-methyl-1,2,3-triazole are reacted according to the procedure of Example 10, 7-(α-amino-p-hydroxyphenylacetamido)-3-(4-methyl-1,2,3-triazol-5-ylthiomethyl)-3-cephem-4-carboxylic acid is obtained.

EXAMPLE 40

7-(p-hydroxymandelamido)cephalosporanic acid

To a solution of p-hydroxymandelic acid (3.0 g, 0.018 mol) in a mixture of dry THF (60 ml) and dry triethylamine (3 ml, 0.021 mol) was added N-trimethylsilylacetamide. The reaction was refluxed for 2 hours under a nitrogen atmosphere. The solution was then cooled to −20° and isobutyl chloroformate (2.7 ml, 0.018 mol) was added over a 20 minute period. After stirring for 20 minutes a solution of 7-ACA (4.89 g, 0.018 mol) in 50% aqueous THF (60 ml) containing triethylamine (3 ml) was added over a 30 minute period at −5° to −10°. The solution was stirred at 0° for 1 hour and at room temperature for 1 hour. The THF was evaporated in vacuo and 3% NaHCO₃ was added to the turbid aqueous layer until it became clear. After the addition of water (50 ml) the solution is extracted with three portions of ether which was discarded. The aqueous phase is cooled, layered with ethyl acetate, and acidified to pH 1.5 with 6N HCl. Phases were separated and the aqueous layer reextracted with ethyl acetate. The combined extracts were washed with water, dried, and evaporated to the title product which was purified as its triethylamine salt.

EXAMPLE 41

When 7-(p-hydroxymandelamido)cephalosporanic acid and any mercaptotriazole or mercaptoimidazole enumerated in Examples 24–35, 37, and 39 are reacted according to the procedure of Example 24 the appropriate 7-(p-hydroxymandelamido)-3-heterocyclicthiomethyl-3-cephem-4-carboxylic acid is obtained. The preferred mercaptoheterocycles are 4-mercapto-1,2,3-triazole and 3-mercapto-1,2,4-triazole. Other preferred heterocycles are 4-methyl-3-mercapto-1,2,4-triazole, 5-methyl-3-mercapto-1,2,4-triazole, 3,4-dimethyl-5-mercapto-1,2,4-triazole, and 4-methyl-5-mercapto-1,2,3-triazole. These products constitute a group of compounds which are 7-(p-hydroxymandelamido)-3-unsubstituted or mono or dialkylsubstituted triazolyl-thiomethyl)-3-cephem-4-carboxylic acids.

We claim:

1. A compound of the formula

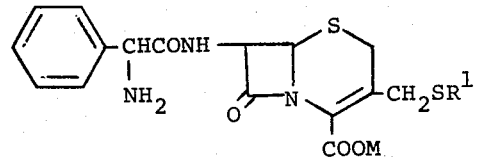

in which
R¹ is 1,2,4-triazolyl, substituted with cyclopropyl, allyl, and methoxymethyl, and
M is hydrogen or an alkali metal,
or a pharmaceutically acceptable salt thereof.

2. A compound according to claim 1, being 7-(α-aminophenylacetamido)-3-(4-allyl-1,2,4-triazol-3-ylthiomethyl)-3-cephem-4-carboxylic acid.

3. A compound according to claim 1, being 7-(α-aminophenylacetamido)-3-(5-cyclopropyl-1,2,4-triazol-3-ylthiomethyl)-3-cephem-4-carboxylic acid.

4. A compound according to claim 1, being 7-(α-aminophenylacetamido)-3-(5-methoxymethyl-1,2,4-triazol-3-ylthiomethyl)-3-cephem-4-carboxylic acid.

* * * * *